US007994194B2

(12) United States Patent
Harbeson

(10) Patent No.: US 7,994,194 B2
(45) Date of Patent: Aug. 9, 2011

(54) 4-OXOQUINOLINE DERIVATIVES

(75) Inventor: Scott L. Harbeson, Cambridge, MA (US)

(73) Assignee: Concert Pharmaceuticals, Inc., Lexington, MA (US)

( * ) Notice: Subject to any disclaimer, the term of this patent is extended or adjusted under 35 U.S.C. 154(b) by 222 days.

(21) Appl. No.: 12/283,620

(22) Filed: Sep. 12, 2008

(65) Prior Publication Data

US 2009/0143427 A1    Jun. 4, 2009

Related U.S. Application Data

(60) Provisional application No. 60/993,428, filed on Sep. 12, 2007.

(51) Int. Cl.
*C07D 215/38*    (2006.01)
*A61K 31/04*    (2006.01)
(52) U.S. Cl. ........................................ 514/312; 546/159
(58) Field of Classification Search .................. 546/159; 514/312
See application file for complete search history.

(56) References Cited

U.S. PATENT DOCUMENTS

| | | | |
|---|---|---|---|
| 6,221,335 B1 | 4/2001 | Foster | |
| 6,440,710 B1 | 8/2002 | Keinan et al. | |
| 6,603,008 B1 | 8/2003 | Ando et al. | |
| 7,176,220 B2 | 2/2007 | Satoh et al. | |
| 7,517,990 B2 | 4/2009 | Ito et al. | |
| 2006/0058286 A1* | 3/2006 | Krystal et al. ............... | 514/220 |
| 2007/0082929 A1 | 4/2007 | Gant et al. | |
| 2007/0197695 A1 | 8/2007 | Potyen et al. | |
| 2008/0103122 A1 | 5/2008 | Veltri | |

FOREIGN PATENT DOCUMENTS

| | | |
|---|---|---|
| WO | WO 95/26325 A2 | 10/1995 |
| WO | WO 2004/046115 A1 | 6/2004 |
| WO | WO 2005/112930 A1 | 12/2005 |
| WO | WO 2005/113509 A1 | 12/2005 |
| WO | 2006/034001 * | 3/2006 |
| WO | WO 2007/089030 A1 | 8/2007 |
| WO | WO 2007/118651 A1 | 10/2007 |
| WO | WO 2009/035662 A1 | 3/2009 |

OTHER PUBLICATIONS

Ekhato, J Labelled Compounds and Radiopharmaceuticals, vol. 48, pp. 179-193, 2005.*
Weiss, Mag Res in Med, vol. 51, pp. 649-654, 2004.*
Fisher, M.B. et al., "The Complexities Inherent in Attempts to Decrease Drug Clearance by Blocking Sites of CYP-Mediated Metabolism," *Curr. Opin. Drug Discov.*, 9(1): 101-109 (Jan. 2006).
Kushner, D.J. et al., "Pharmacological Uses and Perspectives of Heavy Water and Deuterated Compounds," *Can. J. Physiol. Pharmacol.*, 77(2): 79-88 (Feb. 1999).
Sato, M et al., "Novel HIV-1 Integrase Inhibitors Derived from Quinolone Antibiotics," *Journal of Medicinal Chemistry*, 49(5): 1506-1508 (Mar. 5, 2006), XP002507281.
Dec. 30, 2008, International Search Report, PCT/US2008/010662.
Dec. 30, 2008, Written Opinion of the International Searching Authority, PCT/US2008/010662.
Baillie, T. A., "The Use of Stable Isotopes in Pharmacological Research," *Pharmacological Reviews*, 33(2): 81-132 (1981).
Browne, T. R., "Stable Isotope Techniques in Early Drug Development: An Economic Evaluation," *J. Clin. Pharmacol.*, 38: 213-220 (1998).
Cherrah, Y., et al., "Study of Deuterium Isotope Effects on Protein Binding by Gas Chromatography/Mass Spectrometry. Caffeine and Deuterated Isotopomers," *Biomedical and Environmental Mass Spectrometry*, 14: 653-657 (1987).
Dyck, L. E., et al., "Effects of Deuterium Substitution on the Catabolism of β-Phenylethylamine: An In Vivo Study," *Journal of Neurochemistry*, 46(2): 399-404 (1986).
Foster, A. B., "Deuterium Isotope Effects in Studies of Drug Metabolism," *Trends in Pharmacological Sciences*, 5: 524-527 (1984).
Foster, A. B., "Deuterium Isotope Effects in the Metabolism of Drugs and Xenobiotics: Implications for Drug Design," *Advances in Drug Research*, 14: 1-40 (1985).
Gouyette, A., "Synthesis of Deuterium-labelled Elliptinium and its Use in Metabolic Studies," *Biomedical and Environmental Mass Spectrometry*, 15: 243-247 (1988).
Haskins, N. J., "The Application of Stable Isotopes in Biomedical Research," *Biomedical Mass Spectrometry*, 9(7): 269-277 (1982).
Honma S., et al., "The Metabolism of Roxatidine Acetate Hydrochloride," *Drug Metabolism and Disposition*, 15(4): 551-559 (1987).
Pieniaszek, H. J., et al., "Moricizine Bioavailability via Simultaneous, Dual, Stable Isotope Administration: Bioequivalence Implications," *J. Clin. Pharmacol.*, 39: 817-825 (1999).
Tonn G. R., et al., "Simultaneous Analysis of Diphenhydramine and a Stable Isotope Analog ($^2H_{10}$) Diphenhydramine Using Capillary Gas Chromatography with Mass Selective Detection in Biological Fluids from Chronically Instrumented Pregnant Ewes," *Biological Mass Spectrometry*, 22: 633-642 (1993).

(Continued)

*Primary Examiner* — D. Margaret Seaman
(74) *Attorney, Agent, or Firm* — Hamilton, Brook, Smith & Reynolds, P.C.

(57) ABSTRACT

This invention relates to novel compounds that are 4-oxoquinoline derivatives and pharmaceutically acceptable salts thereof. More specifically, this invention relates to novel 4-oxoquinoline derivatives that are derivatives of elvitegravir. This invention also provides pyrogen-free compositions comprising one or more compounds of this invention and a carrier, and the use of the disclosed compounds and compositions in methods of treating diseases and conditions that are beneficially treated by administering an HIV integrase inhibitor, such as elvitegravir.

8 Claims, No Drawings

OTHER PUBLICATIONS

Wolen, R. L., "The Application of Stable Isotopes to Studies of Drug Bioavailability and Bioequivalence," *J. Clin. Pharmacol.*, 26: 419-424 (1986).

Notification Concerning Transmittal of International Preliminary Report on Patentability, Application No. PCT/US2008/010662, date of mailing Mar. 25, 2010.

* cited by examiner

4-OXOQUINOLINE DERIVATIVES

RELATED APPLICATION

This application claims the benefit of U.S. Provisional Application No. 60/993,428, filed on Sep. 12, 2007. The entire teachings of the above application is incorporated herein by reference.

BACKGROUND OF THE INVENTION

AIDS is a chronic, life-threatening condition caused by the human immunodeficiency virus (HIV). It is estimated that over 40 million people are living with HIV/AIDS today (http://www.AIDS.gov). In the United States, there are over 40,000 cases diagnosed each year (http://www.cdc.gov/hiv/).

Elvitegravir, also known as 6-(3-chloro-2-fluorobenzyl)-1-[1(S)-(hydroxymethyl)-2-methylpropyl]-7-methoxy-4-oxo-1,4-dihydroquinoline-3-carboxylic acid, blocks DNA strand transfer through its action as an HIV integrase inhibitor. Elvitegravir is currently in clinical trials for treatment of HIV infection.

Despite the beneficial activities of elvitegravir, there is a continuing need for new compounds to treat the aforementioned diseases and conditions.

SUMMARY OF THE INVENTION

This invention relates to novel compounds that are 4-oxoquinoline derivatives and pharmaceutically acceptable salts thereof. More specifically, this invention relates to novel 4-oxoquinoline derivatives that are derivatives of elvitegravir. This invention also provides pyrogen-free compositions comprising one or more compounds of this invention and a carrier, and the use of the disclosed compounds and compositions in methods of treating diseases and conditions that are beneficially treated by administering an HIV integrase inhibitor, such as elvitegravir.

DETAILED DESCRIPTION OF THE INVENTION

The terms "ameliorate" and "treat" are used interchangeably and include both therapeutic and prophylactic treatment. Both terms mean decrease, suppress, attenuate, diminish, arrest, or stabilize the development or progression of a disease (e.g., a disease or disorder delineated herein), lessen the severity of the disease or improve the symptoms associated with the disease.

"Disease" means any condition or disorder that damages or interferes with the normal function of a cell, tissue, or organ.

It will be recognized that some variation of natural isotopic abundance occurs in a synthesized compound depending upon the origin of chemical materials used in the synthesis. Thus, a preparation of elvitegravir will inherently contain small amounts of deuterated isotopologues. The concentration of naturally abundant stable hydrogen and carbon isotopes, notwithstanding this variation, is small and immaterial as compared to the degree of stable isotopic substitution of compounds of this invention. See, for instance, Wada E et al., Seikagaku 1994, 66:15; Ganes L Z et al., Comp Biochem Physiol Mol Integr Physiol 1998, 119:725. In a compound of this invention, when a particular position is designated as having deuterium, it is understood that the abundance of deuterium at that position is substantially greater than the natural abundance of deuterium, which is 0.015%. A position designated as having deuterium typically has a minimum isotopic enrichment factor of at least 3340 (50.1% deuterium incorporation) at each atom designated as deuterium in said compound.

The term "isotopic enrichment factor" as used herein means the ratio between the isotopic abundance and the natural abundance of a specified isotope.

In other embodiments, a compound of this invention has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

In the compounds of this invention any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Also unless otherwise stated, when a position is designated specifically as "D" or "deuterium", the position is understood to have deuterium at an abundance that is at least 3340 times greater than the natural abundance of deuterium, which is 0.015% (i.e., at least 50.1% incorporation of deuterium).

The term "isotopologue" refers to a species that differs from a specific compound of this invention only in the isotopic composition thereof.

The term "compound," as used in reference to compounds of the invention, refers to a collection of molecules having an identical chemical structure, except that there may be isotopic variation among the constituent atoms of the molecules. Thus, it will be clear to those of skill in the art that a compound represented by a particular chemical structure containing indicated deuterium atoms, will also contain lesser amounts of isotopologues having hydrogen atoms at one or more of the designated deuterium positions in that structure. The relative amount of such isotopologues in a compound of this invention will depend upon a number of factors including the isotopic purity of deuterated reagents used to make the compound and the efficiency of incorporation of deuterium in the various synthesis steps used to prepare the compound. However, as set forth above the relative amount of such isotopologues will be less than 49.9% of the compound.

A salt of a compound of this invention is formed between an acid and a basic group of the compound, such as an amino functional group, or a base and an acidic group of the compound, such as a carboxyl functional group. According to another embodiment, the compound is a pharmaceutically acceptable acid addition salt.

The term "pharmaceutically acceptable," as used herein, refers to a component that is, within the scope of sound medical judgment, suitable for use in contact with the tissues of humans and other mammals without undue toxicity, irritation, allergic response and the like, and are commensurate with a reasonable benefit/risk ratio. A "pharmaceutically acceptable salt" means any non-toxic salt that, upon administration to a recipient, is capable of providing, either directly or indirectly, a compound of this invention. A "pharmaceutically acceptable counterion" is an ionic portion of a salt that is not toxic when released from the salt upon administration to a recipient.

Acids commonly employed to form pharmaceutically acceptable salts include inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephathalate, sulfonate, xylene sulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and other salts. In one embodiment, pharmaceutically acceptable acid addition salts include those formed with mineral acids such as hydrochloric acid and hydrobromic acid, and especially those formed with organic acids such as maleic acid.

The compounds of the present invention (e.g., compounds of Formula I), may contain an asymmetric carbon atom, for example, as the result of deuterium substitution or otherwise. As such, compounds of this invention can exist as either individual enantiomers, or mixtures of the two enantiomers. Accordingly, a compound of the present invention may exist as either a racemic mixture or a scalemic mixture, or as individual respective stereoisomers that are substantially free from another possible stereoisomer. The term "substantially free of other stereoisomers" as used herein means less than 25% of other stereoisomers, preferably less than 10% of other stereoisomers, more preferably less than 5% of other stereoisomers and most preferably less than 2% of other stereoisomers, or less than "X"% of other stereoisomers (wherein X is a number between 0 and 100, inclusive) are present. Methods of obtaining or synthesizing an individual enantiomer for a given compound are known in the art and may be applied as practicable to final compounds or to starting material or intermediates.

Unless otherwise indicated, when a disclosed compound is named or depicted by a structure without specifying the stereochemistry and has one or more chiral centers, it is understood to represent all possible stereoisomers of the compound.

The term "stable compounds," as used herein, refers to compounds which possess stability sufficient to allow for their manufacture and which maintain the integrity of the compound for a sufficient period of time to be useful for the purposes detailed herein (e.g., formulation into therapeutic products, intermediates for use in production of therapeutic compounds, isolatable or storable intermediate compounds, treating a disease or condition responsive to therapeutic agents).

"D" refers to deuterium. "Stereoisomer" refers to both enantiomers and diastereomers. "Tert", "t", and "t-" each refer to tertiary. "US" refers to the United States of America.

Throughout this specification, a variable may be referred to generally (e.g., "each R") or may be referred to specifically (e.g., $R^1$, $R^2$, $R^3$, etc.). Unless otherwise indicated, when a variable is referred to generally, it is meant to include all specific embodiments of that particular variable.

Therapeutic Compounds

The present invention provides a compound of Formula I:

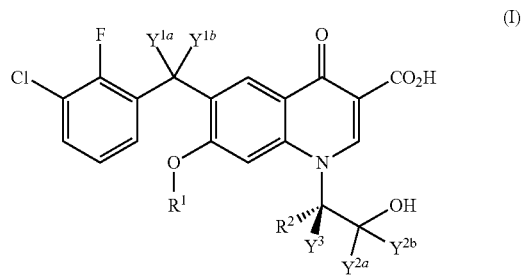

or a pharmaceutically acceptable salt thereof, wherein:

each Y is independently selected from hydrogen and deuterium;

$R^1$ is selected from $CH_3$, $CH_2D$, $CHD_2$ and $CD_3$;

$R^2$ is an isopropyl group optionally containing 1 to 7 deuterium atoms; and when each Y is hydrogen, at least one R contains a deuterium atom.

Other embodiments include a compound of formula I, wherein:

a) $R^1$ is selected from $CH_3$ and $CD_3$;

b) $R^2$ is selected from —$CH(CH_3)_2$, —$CD(CH_3)_2$, —$CH(CD_3)_2$ and —$CD(CD_3)_2$;

c) $Y^{1a}$ and $Y^{1b}$ are the same; or d) $Y^{2a}$ and $Y^{2b}$ are the same.

Still other embodiments include a compound of formula I, having at least two of the features set forth in a) through d), above. Examples include, but are not limited to: a and b; a and c; b and c; and a, b and c.

More specific embodiments include a compound of formula I, wherein:

e) $R^1$ is $CD_3$;

f) $R^2$ is selected from —$CH(CH_3)_2$ and —$CD(CD_3)_2$;

g) $Y^{1a}$ and $Y^{1b}$ are deuterium; or h) $Y^{2a}$ and $Y^{2b}$ are deuterium.

Additional specific embodiments include a compound of formula I, having at least two of the features set forth in e) through h), above. Examples include, but are not limited to: e and f; e and g; f and g; e and h; f and h; e, f and h; and e, f and g.

Still other specific embodiments include a compound of formula I, having at least one of the features set forth in a) through d), above for one variable (i.e., $R^1$, $R^2$, $Y^1$ and $Y^2$); and one of the features set forth in e) through h), above for a different variable. Examples include, but are not limited to: a and f; a and g; a and h; b and g; b and h; c and f; c and h; e and b; e and g; e and h; f and g; f and h; a, f and c; a, b and g; a, f and g; a, b and h; a, f and h; a, c and h; b, c and h; e, b and c; e, f and c; e, b and g; e, b and h; e, c and h; f, c and h; a, b, c and h; a, f, c and h; and e, b, c and h.

Examples of specific compounds of Formula I are shown in Table 1 below.

TABLE 1

Exemplary Embodiments of Formula I

| Compound | $R^1$ | $R^2$ | $Y^{1a}$ | $Y^{1b}$ | $Y^{2a}$ | $Y^{2b}$ | $Y^3$ |
|---|---|---|---|---|---|---|---|
| 100 | $CD_3$ | $(CH_3)_2CH-$ | D | D | H | H | H |
| 101 | $CD_3$ | $(CH_3)_2CH-$ | H | H | D | D | H |
| 102 | $CD_3$ | $(CH_3)_2CH-$ | D | D | D | D | H |
| 103 | $CD_3$ | $(CH_3)_2CH-$ | D | D | H | H | D |
| 104 | $CD_3$ | $(CH_3)_2CH-$ | H | H | D | D | D |
| 105 | $CD_3$ | $(CH_3)_2CH-$ | D | D | D | D | D |
| 106 | $CH_3$ | $(CD_3)_2CD-$ | D | D | H | H | D |
| 107 | $CH_3$ | $(CD_3)_2CD-$ | H | H | D | D | D |
| 108 | $CH_3$ | $(CD_3)_2CD-$ | D | D | D | D | D |
| 109 | $CD_3$ | $(CD_3)_2CD-$ | D | D | H | H | D |
| 110 | $CD_3$ | $(CD_3)_2CD-$ | H | H | D | D | D |
| 111 | $CD_3$ | $(CD_3)_2CD-$ | D | D | D | D | D |
| 112 | $CD_3$ | $(CH_3)_2CH-$ | H | H | H | H | H |

In another set of embodiments, any atom not designated as deuterium in any of the embodiments set forth above is present at its natural isotopic abundance.

The synthesis of compounds of Formula I can be readily achieved by synthetic chemists of ordinary skill. Relevant procedures and intermediates are disclosed, for instance in PCT patent publications WO2005/113509 and WO 2004/046115; and in U.S. Pat. No. 7,176,220.

Such methods can be carried out utilizing corresponding deuterated and optionally, other isotope-containing reagents and/or intermediates to synthesize the compounds delineated herein, or invoking standard synthetic protocols known in the art for introducing isotopic atoms to a chemical structure. Certain intermediates can be used with or without purification (e.g., filtration, distillation, sublimation, crystallization, trituration, solid phase extraction, and chromatography).

Exemplary Synthesis

Compounds of this invention may be prepared as illustrated in the routes shown below.

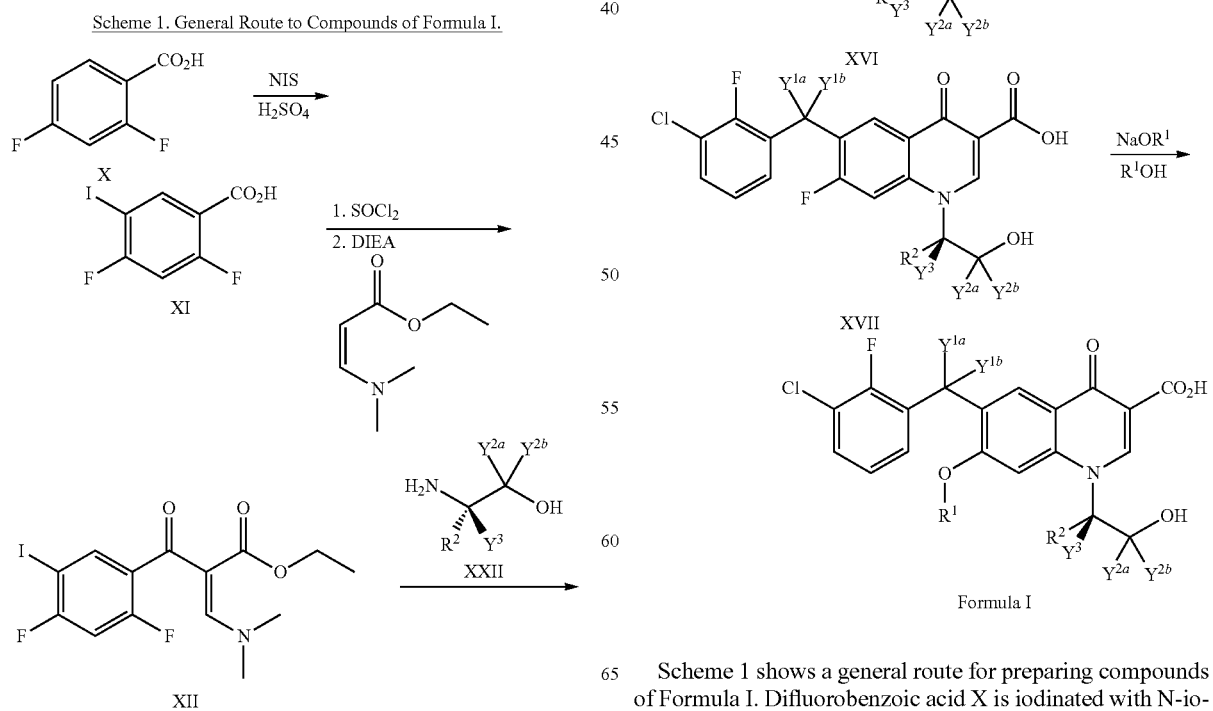

Scheme 1 shows a general route for preparing compounds of Formula I. Difluorobenzoic acid X is iodinated with N-iodosuccinimide in sulfuric acid to provide XI, which is then converted in situ to the acid chloride and treated with the dimethylamino acrylate ester to provide XII. Compound XII is treated with the appropriate substituted valinol XXII to yield XIII. Cyclization in the presence of potassium carbonate yields XIV, which is then protected as the methyl carbonate XV by reaction with methyl chloroformate. Conversion of the appropriately substituted benzyl bromide XX to the zinc bromide followed by Negishi coupling yields XVI, which is then deprotected to XVII with aqueous sodium hydroxide. Displacement of the fluoride with the appropriate alkoxide provides compounds of Formula I.

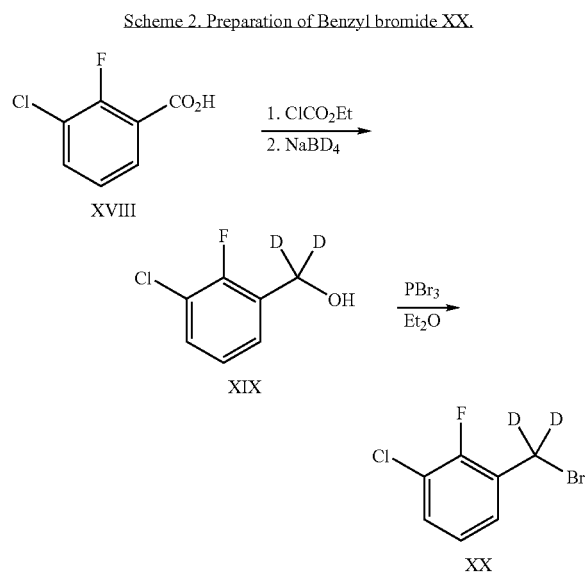

Scheme 2 shows the preparation of benzyl bromide XX. Commercially available benzoic acid XVIII may be reduced to the $d_2$-benzyl alcohol XIX using the method of Kikuo, I et al., Chem Pharm Bull, 1968, 16: 492-497 by substituting sodium borodeuteride for sodium borohydride. Benzylic alcohols such as XIX can be readily converted to benzylic bromides according to the methods described by Naganawa, A et al., Bioorg Med Chem, 2006, 14: 7774-7789; and Chesta, C A et al., JACS, 2007, 129: 5012-5022, which provides XX, wherein $Y^{1a}$ and $Y^{1b}$ are simultaneously deuterium.

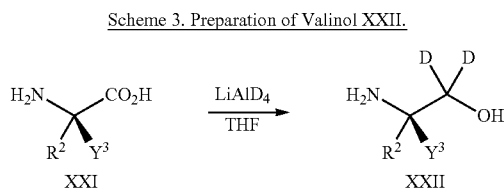

Scheme 3 shows the preparation of valinol XXII. Reduction of valine (XXI) to $d_2$-valinol XXII with lithium aluminum deuteride is described by Boyd, E et al., Tet Asym, 2007, 17: 3406-3422 and produces a reagent wherein $Y^{2a}$ and $Y^{2b}$ are simultaneously deuterium. This method may also be used to convert other appropriately-deuterated valines XXI to other deuterated versions of XXII.

The specific approaches and compounds shown above are not intended to be limiting. The chemical structures in the schemes herein depict variables that are hereby defined commensurately with chemical group definitions (moieties, atoms, etc.) of the corresponding position in the compound formulae herein, whether identified by the same variable name (i.e., $R^1$, $R^2$, $R^3$, etc.) or not. The suitability of a chemical group in a compound structure for use in the synthesis of another compound is within the knowledge of one of ordinary skill in the art. Additional methods of synthesizing compounds of Formula I and their synthetic precursors, including those within routes not explicitly shown in schemes herein, are within the means of chemists of ordinary skill in the art. Methods for optimizing reaction conditions and, if necessary, minimizing competing by-products, are known in the art. In addition to the synthetic references cited herein, reaction schemes and protocols may be determined by the skilled artisan by use of commercially available structure-searchable database software, for instance, SciFinder® (CAS division of the American Chemical Society), STN® (CAS division of the American Chemical Society), CrossFire Beilstein® (Elsevier MDL), or internet search engines such as Google® or keyword databases such as the US Patent and Trademark Office text database.

The methods described herein may also additionally include steps, either before or after the steps described specifically herein, to add or remove suitable protecting groups in order to ultimately allow synthesis of the compounds herein. In addition, various synthetic steps may be performed in an alternate sequence or order to give the desired compounds. Synthetic chemistry transformations and protecting group methodologies (protection and deprotection) useful in synthesizing the applicable compounds are known in the art and include, for example, those described in Larock R, *Comprehensive Organic Transformations*, VCH Publishers (1989); Greene T W et al., *Protective Groups in Organic Synthesis*, $3^{rd}$ Ed., John Wiley and Sons (1999); Fieser L et al., *Fieser and Fieser's Reagents for Organic Synthesis*, John Wiley and Sons (1994); and Paquette L, ed., *Encyclopedia of Reagents for Organic Synthesis*, John Wiley and Sons (1995) and subsequent editions thereof.

Combinations of substituents and variables envisioned by this invention are only those that result in the formation of stable compounds.

Compositions

The invention also provides pyrogen-free compositions comprising an effective amount of a compound of Formula I (e.g., including any of the formulae herein), or a pharmaceutically acceptable salt of said compound; and an acceptable carrier. Preferably, a composition of this invention is formulated for pharmaceutical use ("a pharmaceutical composition"), wherein the carrier is a pharmaceutically acceptable carrier. The carrier(s) are "acceptable" in the sense of being compatible with the other ingredients of the formulation and, in the case of a pharmaceutically acceptable carrier, not deleterious to the recipient thereof in an amount used in the medicament.

Pharmaceutically acceptable carriers, adjuvants and vehicles that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

If required, the solubility and bioavailability of the compounds of the present invention in pharmaceutical compositions may be enhanced by methods well-known in the art. One method includes the use of lipid excipients in the formulation. See "Oral Lipid-Based Formulations: Enhancing the Bioavailability of Poorly Water-Soluble Drugs (Drugs and the Pharmaceutical Sciences)," David J. Hauss, ed. Informa Healthcare, 2007; and "Role of Lipid Excipients in Modifying Oral and Parenteral Drug Delivery: Basic Principles and Biological Examples," Kishor M. Wasan, ed. Wiley-Interscience, 2006.

Another known method of enhancing bioavailability is the use of an amorphous form of a compound of this invention optionally formulated with a poloxamer, such as LUTROL™ and PLURONIC™ (BASF Corporation), or block copolymers of ethylene oxide and propylene oxide. See U.S. Pat. No. 7,014,866; and United States patent publications 20060094744 and 20060079502.

The pharmaceutical compositions of the invention include those suitable for oral, rectal, nasal, topical (including buccal and sublingual), vaginal or parenteral (including subcutaneous, intramuscular, intravenous and intradermal) administration. In certain embodiments, the compound of the formulae herein is administered transdermally (e.g., using a transdermal patch or iontophoretic techniques). Other formulations may conveniently be presented in unit dosage form, e.g., tablets, sustained release capsules, and in liposomes, and may be prepared by any methods well known in the art of pharmacy. See, for example, Remington's Pharmaceutical Sciences, Mack Publishing Company, Philadelphia, Pa. (17th ed. 1985).

Such preparative methods include the step of bringing into association with the molecule to be administered ingredients such as the carrier that constitutes one or more accessory ingredients. In general, the compositions are prepared by uniformly and intimately bringing into association the active ingredients with liquid carriers, liposomes or finely divided solid carriers, or both, and then, if necessary, shaping the product.

In certain embodiments, the compound is administered orally. Compositions of the present invention suitable for oral administration may be presented as discrete units such as capsules, sachets, or tablets each containing a predetermined amount of the active ingredient; a powder or granules; a solution or a suspension in an aqueous liquid or a non-aqueous liquid; an oil-in-water liquid emulsion; a water-in-oil liquid emulsion; packed in liposomes; or as a bolus, etc. Soft gelatin capsules can be useful for containing such suspensions, which may beneficially increase the rate of compound absorption.

In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are administered orally, the active ingredient is combined with emulsifying and suspending agents. If desired, certain sweetening and/or flavoring and/or coloring agents may be added.

Compositions suitable for oral administration include lozenges comprising the ingredients in a flavored basis, usually sucrose and acacia or tragacanth; and pastilles comprising the active ingredient in an inert basis such as gelatin and glycerin, or sucrose and acacia.

Compositions suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets.

Such injection solutions may be in the form, for example, of a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant.

The pharmaceutical compositions of this invention may be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. See, e.g.: Rabinowitz J D and Zaffaroni A C, U.S. Pat. No. 6,803,031, assigned to Alexza Molecular Delivery Corporation.

Topical administration of the pharmaceutical compositions of this invention is especially useful when the desired treatment involves areas or organs readily accessible by topical application. For topical application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax, and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol, and water. The pharmaceutical compositions of this invention may also be topically applied to the lower intestinal tract by rectal suppository formulation or in a suitable enema formulation. Topically-transdermal patches and iontophoretic administration are also included in this invention.

Application of the subject therapeutics may be local, so as to be administered at the site of interest. Various techniques can be used for providing the subject compositions at the site of interest, such as injection, use of catheters, trocars, projectiles, pluronic gel, stents, sustained drug release polymers or other device which provides for internal access.

Thus, according to yet another embodiment, the compounds of this invention may be incorporated into compositions for coating an implantable medical device, such as prostheses, artificial valves, vascular grafts, stents, or catheters. Suitable coatings and the general preparation of coated implantable devices are known in the art and are exemplified in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition. Coatings for invasive devices are to be included within the definition of pharmaceutically acceptable carrier, adjuvant or vehicle, as those terms are used herein.

According to another embodiment, the invention provides a method of coating an implantable medical device comprising the step of contacting said device with the coating composition described above. It will be obvious to those skilled in the art that the coating of the device will occur prior to implantation into a mammal.

According to another embodiment, the invention provides a method of impregnating an implantable drug release device comprising the step of contacting said drug release device with a compound or composition of this invention. Implantable drug release devices include, but are not limited to, biodegradable polymer capsules or bullets, non-degradable, diffusible polymer capsules and biodegradable polymer wafers.

According to another embodiment, the invention provides an implantable medical device coated with a compound or a composition comprising a compound of this invention, such that said compound is therapeutically active.

According to another embodiment, the invention provides an implantable drug release device impregnated with or containing a compound or a composition comprising a compound of this invention, such that said compound is released from said device and is therapeutically active.

Where an organ or tissue is accessible because of removal from the patient, such organ or tissue may be bathed in a medium containing a composition of this invention, a composition of this invention may be painted onto the organ, or a composition of this invention may be applied in any other convenient way.

In another embodiment, a composition of this invention further comprises a second therapeutic agent. The second therapeutic agent may be selected from any compound or therapeutic agent known to have or that demonstrates advantageous properties when administered with a compound having the same mechanism of action as elvitegravir. Such agents include those indicated as being useful in combination with elvitegravir, including but not limited to, those described in WO 2005112930.

Preferably, the second therapeutic agent is an agent useful in the treatment or prevention of HIV infection.

In one embodiment, the second therapeutic agent is selected from ritonavir, darunavir, tipranavir and combinations thereof.

In another embodiment, the invention provides separate dosage forms of a compound of this invention and one or more of any of the above-described second therapeutic agents, wherein the compound and second therapeutic agent are associated with one another. The term "associated with one another" as used herein means that the separate dosage forms are packaged together or otherwise attached to one another such that it is readily apparent that the separate dosage forms are intended to be sold and administered together (within less than 24 hours of one another, consecutively or simultaneously).

In the pharmaceutical compositions of the invention, the compound of the present invention is present in an effective amount. As used herein, the term "effective amount" refers to an amount which, when administered in a proper dosing regimen, is sufficient to treat (therapeutically or prophylactically) the target disorder. For example, an effective amount is sufficient to reduce or ameliorate the severity, duration or progression of the disorder being treated, prevent the advancement of the disorder being treated, cause the regression of the disorder being treated, or enhance or improve the prophylactic or therapeutic effect(s) of another therapy.

The interrelationship of dosages for animals and humans (based on milligrams per meter squared of body surface) is described in Freireich et al., (1966) Cancer Chemother. Rep 50: 219. Body surface area may be approximately determined from height and weight of the patient. See, e.g., Scientific Tables, Geigy Pharmaceuticals, Ardsley, N.Y., 1970, 537.

In one embodiment, an effective amount of a compound of this invention can range from about 0.5 mg to about 8000 mg per treatment. In more specific embodiments the range is from about 5 to 4000 mg, or from 10 to 1600 mg, or most specifically from 50 to 800 mg per treatment. Treatment typically is administered one to two times daily.

Effective doses will also vary, as recognized by those skilled in the art, depending on the diseases treated, the severity of the disease, the route of administration, the sex, age and general health condition of the patient, excipient usage, the possibility of co-usage with other therapeutic treatments such as use of other agents and the judgment of the treating physician. For example, guidance for selecting an effective dose can be determined by reference to the prescribing information for elvitegravir.

For pharmaceutical compositions that comprise a second therapeutic agent, an effective amount of the second therapeutic agent is between about 20% and 100% of the dosage normally utilized in a monotherapy regime using just that agent. Preferably, an effective amount is between about 70% and 100% of the normal monotherapeutic dose. The normal monotherapeutic dosages of these second therapeutic agents are well known in the art. See, e.g., Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), each of which references are incorporated herein by reference in their entirety.

It is expected that some of the second therapeutic agents referenced above will act synergistically with the compounds of this invention. When this occurs, it will allow the effective dosage of the second therapeutic agent and/or the compound of this invention to be reduced from that required in a monotherapy. This has the advantage of minimizing toxic side effects of either the second therapeutic agent of a compound of this invention, synergistic improvements in efficacy, improved ease of administration or use and/or reduced overall expense of compound preparation or formulation.

Methods of Treatment

In another embodiment, the invention provides a method of inhibiting the activity of HIV integrase in a cell infected with HIV, comprising contacting the cell with one or more compounds of Formula I herein.

According to another embodiment, the invention provides a method of treating a disease that is beneficially treated by elvitegravir in a patient in need thereof comprising the step of administering to said patient an effective amount of a compound or a composition of this invention. Such diseases are well known in the art and are disclosed in, but not limited to the following patents and published applications: WO 2005113509, and WO 2007089030. Such diseases include, but are not limited to, HIV infection.

In one particular embodiment, the method of this invention is used to treat HIV infection in a patient in need thereof.

Methods delineated herein also include those wherein the patient is identified as in need of a particular stated treatment. Identifying a patient in need of such treatment can be in the judgment of a patient or a health care professional and can be subjective (e.g. opinion) or objective (e.g. measurable by a test or diagnostic method).

In another embodiment, any of the above methods of treatment comprises the further step of co-administering to said patient one or more second therapeutic agents. The choice of second therapeutic agent may be made from any second therapeutic agent known to be useful for co-administration with elvitegravir. The choice of second therapeutic agent is also dependent upon the particular disease or condition to be treated. Examples of second therapeutic agents that may be employed in the methods of this invention are those set forth above for use in combination compositions comprising a compound of this invention and a second therapeutic agent.

In particular, the combination therapies of this invention include co-administering a compound of Formula I and a second therapeutic agent for treatment of the following conditions: HIV infection (ritonavir, darunavir, tipranavir or any combination thereof).

The term "co-administered" as used herein means that the second therapeutic agent may be administered together with a compound of this invention as part of a single dosage form (such as a composition of this invention comprising a compound of the invention and an second therapeutic agent as described above) or as separate, multiple dosage forms. Alternatively, the additional agent may be administered prior to, consecutively with, or following the administration of a compound of this invention. In such combination therapy treatment, both the compounds of this invention and the second therapeutic agent(s) are administered by conventional methods. The administration of a composition of this invention, comprising both a compound of the invention and a second therapeutic agent, to a patient does not preclude the separate administration of that same therapeutic agent, any other second therapeutic agent or any compound of this invention to said patient at another time during a course of treatment.

Effective amounts of these second therapeutic agents are well known to those skilled in the art and guidance for dosing may be found in patents and published patent applications referenced herein, as well as in Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), and other medical texts. However, it is well within the skilled artisan's purview to determine the second therapeutic agent's optimal effective-amount range.

In one embodiment of the invention, where a second therapeutic agent is administered to a subject, the effective amount of the compound of this invention is less than its effective amount would be where the second therapeutic agent is not administered. In another embodiment, the effective amount of the second therapeutic agent is less than its effective amount would be where the compound of this invention is not administered. In this way, undesired side effects associated with high doses of either agent may be minimized. Other potential advantages (including without limitation improved dosing regimens and/or reduced drug cost) will be apparent to those of skill in the art.

In yet another aspect, the invention provides the use of a compound of Formula I alone or together with one or more of the above-described second therapeutic agents in the manufacture of a medicament, either as a single composition or as separate dosage forms, for treatment or prevention in a patient of a disease, disorder or symptom set forth above. Another aspect of the invention is a compound of Formula I for use in the treatment or prevention in a patient of a disease, disorder or symptom thereof delineated herein.

Diagnostic Methods and Kits

The compounds and compositions of this invention are also useful as reagents in methods for determining the concentration of elvitegravir in solution or biological sample such as plasma, examining the metabolism of elvitegravir and other analytical studies.

According to one embodiment, the invention provides a method of determining the concentration, in a solution or a biological sample, of elvitegravir, comprising the steps of:
a) adding a known concentration of a compound of Formula I to the solution of biological sample;
b) subjecting the solution or biological sample to a measuring device that distinguishes elvitegravir from a compound of Formula I;
c) calibrating the measuring device to correlate the detected quantity of the compound of Formula I with the known concentration of the compound of Formula I added to the biological sample or solution; and
d) measuring the quantity of elvitegravir in the biological sample with said calibrated measuring device; and
e) determining the concentration of elvitegravir in the solution of sample using the correlation between detected quantity and concentration obtained for a compound of Formula I.

Measuring devices that can distinguish elvitegravir from the corresponding compound of Formula I include any measuring device that can distinguish between two compounds that differ from one another only in isotopic abundance. Exemplary measuring devices include a mass spectrometer, NMR spectrometer, or IR spectrometer.

In another embodiment, the invention provides a method of evaluating the metabolic stability of a compound of Formula I comprising the steps of contacting the compound of Formula I with a metabolizing enzyme source for a period of time and comparing the amount of the compound of Formula I with the metabolic products of the compound of Formula I after the period of time.

In a related embodiment, the invention provides a method of evaluating the metabolic stability of a compound of Formula I in a patient following administration of the compound of Formula I. This method comprises the steps of obtaining a serum, urine or feces sample from the patient at a period of time following the administration of the compound of Formula I to the subject; and comparing the amount of the compound of Formula I with the metabolic products of the compound of Formula I in the serum, urine or feces sample.

The present invention also provides kits for use to treat HIV infection. These kits comprise (a) a pharmaceutical composition comprising a compound of Formula I or a salt thereof, wherein said pharmaceutical composition is in a container; and (b) instructions describing a method of using the pharmaceutical composition to treat HIV infection.

The container may be any vessel or other sealed or sealable apparatus that can hold said pharmaceutical composition. Examples include bottles, ampules, divided or multi-chambered holders bottles, wherein each division or chamber comprises a single dose of said composition, a divided foil packet wherein each division comprises a single dose of said composition, or a dispenser that dispenses single doses of said composition. The container can be in any conventional shape or form as known in the art which is made of a pharmaceutically acceptable material, for example a paper or cardboard box, a glass or plastic bottle or jar, a re-sealable bag (for example, to hold a "refill" of tablets for placement into a different container), or a blister pack with individual doses for pressing out of the pack according to a therapeutic schedule. The container employed can depend on the exact dosage form involved, for example a conventional cardboard box would not generally be used to hold a liquid suspension. It is feasible that more than one container can be used together in a single package to market a single dosage form. For example, tablets may be contained in a bottle, which is in turn contained within a box. In one embodiment, the container is a blister pack. The kits of this invention may also comprise a device to administer or to measure out a unit dose of the pharmaceutical composition. Such device may include an inhaler if said composition is an inhalable composition; a syringe and needle if said composition is an injectable composition; a syringe, spoon, pump, or a vessel with or without volume markings if said composition is an oral liquid composition; or any other measuring or delivery device appropriate to the dosage formulation of the composition present in the kit.

In certain embodiment, the kits of this invention may comprise in a separate vessel of container a pharmaceutical composition comprising a second therapeutic agent, such as one of those listed above for use for co-administration with a compound of this invention.

EXAMPLES

Example 1

Synthesis of (S)-6-(3-Chloro-2-fluorobenzyl)-1-(1-hydroxy-3-methylbutan-2-yl)-7-(methoxy-d$_3$)-4-oxo-1,4-dihydroquinoline-3-carboxylic acid (112)

Compound 112 was prepared as outlined in Scheme 4 below. Details of the synthesis are set forth below.

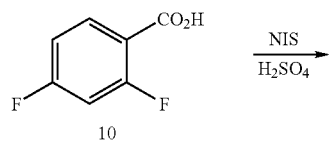

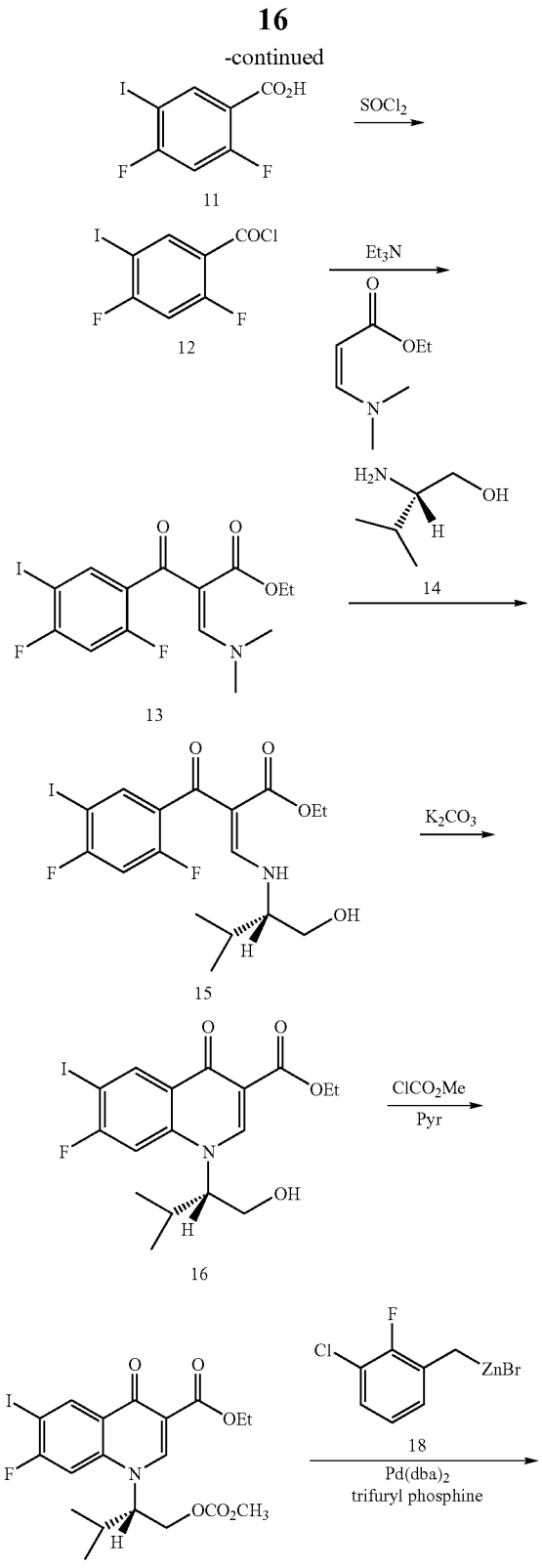

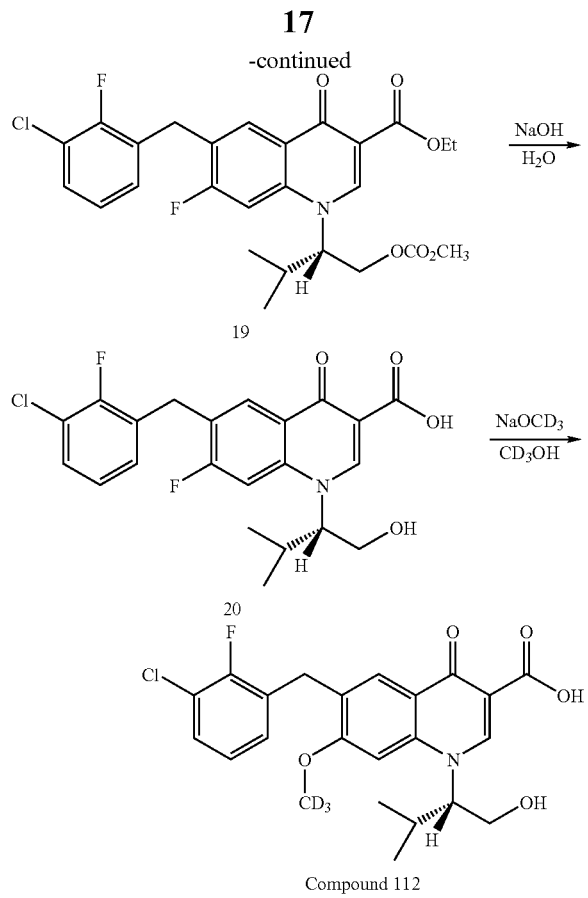

Compound 112

Synthesis of 2,4-Difluoro-5-iodobenzoic acid (11). 2,4-Difluorobenzoic acid 10 (45.0 g, 285 mmol) was dissolved in concentrated sulfuric acid (360 mL) at 0° C. and N-iodosuccinimide (NIS, 64 g, 284 mmol) was added in portions at 0° C. The mixture was allowed to warm to room temperature (rt) and stirred 4 hours (h). The mixture was poured into ice water (approximately 1000 mL) and 10% aqueous sodium carbonate solution (80 mL) was added. After the mixture was stirred for 0.5 h, the precipitate was filtered, washed with water (approximately 2000 mL), then dried at 50° C. in a convection oven for 2 days to provide 76.3 g (94%) of 11 as a gray solid.

Synthesis of 2,4-Difluoro-5-iodobenzoyl chloride (12). To a solution of 11 (74.0 g, 260 mmol) in toluene (370 mL) was added thionyl chloride (95 mL, 1300 mmol) in DMF (2.5 mL, 26 mmol) and the mixture was heated to reflux for 4 h. The mixture was cooled to approximately 60° C. and filtered to remove insoluble material. The filtrate was concentrated under reduced pressure and residual thionyl chloride was co-evaporated with toluene (2×120 mL) to give crude 12 which was used without purification.

Synthesis of (Z)-Ethyl 2-(2,4-difluoro-5-iodobenzoyl)-3-(dimethylamino)acrylate (13). Crude 12 was dissolved in THF (185 mL) and the solution was added dropwise to a solution of ethyl 3-dimethylaminoacrylate (41.0 g, 286 mmol) and triethylamine (44 mL, 316 mmol) in THF (185 mL). When addition was complete the mixture was heated to reflux for 5 h. The mixture was cooled to rt and concentrated under reduced pressure to give a brown solid. The crude product was triturated with MTBE to give 65.2 g (61%) of 13 as a gray solid.

Synthesis of (S,Z)-Ethyl 2-(2,4-difluoro-5-iodobenzoyl)-3-(1-hydroxy-3-methylbutan-2-ylamino)acrylate (15). A solution of 13 (14.6 g, 35.6 mmol) and (S)-2-amino-3-methylbutan-1-ol (14) (3.95 g, 36.7 mmol) in THF (35 mL) was stirred at rt for 30 minutes (min). The mixture was concentrated under reduced pressure to give crude 15 as a yellow oil which was used without further purification.

Synthesis of (S)-Ethyl 7-fluoro-1-(1-hydroxy-3-methylbutan-2-yl)-6-iodo-4-oxo-1,4-dihydroquinoline-3-carboxylate (16). Potassium carbonate (5.0 g, 36.2 mmol) was added to crude 15 dissolved in DMF (36 mL). The resulting mixture was stirred at rt for 22 h. Water (120 mL) was added and the mixture was stirred for 0.5 h. The precipitate was filtered, washed with water (120 mL) and EtOAc (20 mL). The solid was suspended in EtOAc (70 mL) and stirred for 30 min. The precipitate was filtered, suspended in MTBE (70 mL) and stirred for 30 min. The solid was filtered and dried in a vacuum oven to give 13.4 g (85%, greater than 98% purity) of 16 as an off-white solid.

Synthesis of (S)-Ethyl 7-fluoro-6-iodo-1-(1-(methoxycarbonyloxy)-3-methylbutan-2-yl)-4-oxo-1,4-dihydroquinoline-3-carboxylate (17). To a solution of 16 (13.4 g, 29.9 mmol) and pyridine (9.7 mL, 120 mmol) in anhydrous chloroform (60 mL) at 0° C. was added dropwise a solution of methyl chloroformate (9.2 mL, 120 mmol) in chloroform (30 mL). The mixture was stirred 1 h at 0° C., and then was washed with 2 N HCl (2×60 mL). The organic phase was dried over $Na_2SO_4$, filtered and concentrated under reduced pressure to give a yellow oil. The oil (mixture of 16 and 17) was treated with pyridine (5 mL, 62 mmol) and methyl chloroformate (4.6 mL, 60 mmol) under the same conditions above another four times to achieve approximately 90% conversion. The crude product, a yellow oil, was purified on an AnaLogix chromatography system with 33-50% EtOAc/heptanes to give 7.6 g (50%, greater than 98% purity) of 17 as a colorless oil.

Synthesis of (S)-Ethyl 6-(3-chloro-2-fluorobenzyl)-7-fluoro-1-(1-(methoxycarbonyloxy)-3-methylbutan-2-yl)-4-oxo-1,4-dihydroquinoline-3-carboxylate (19). A solution of dibromoethane (0.01 mL, 0.11 mmol) and 1M TMSCl in THF (0.2 mL, 0.2 mmol) was added to a mixture of Zn (200 mg, 3.06 mmol) in THF (5 mL) at rt and the resulting mixture was heated at 65° C. for 0.5 h. The mixture was then cooled to rt and a solution of 3-chloro-2-fluorobenzyl bromide (700 mg, 3.13 mmol) in THF (10 mL) was added with stirring continuing until all Zn had dissolved (approximately 1.5 hr). To the resulting gray slurry of (3-chloro-2-fluorobenzyl)zinc(II) bromide 18 was added a solution of 17 (1.22 g, 2.4 mmol), $Pd(dba)_2$ (70 mg, 0.12 mmol) and trifurylphosphine (56 mg, 0.24 mmol) in THF (5 mL), and the reaction mixture was stirred at 60° C. for approximately 0.5 h. The mixture was cooled to rt, saturated aqueous ammonium chloride (25 mL) was added to quench the reaction and the mixture was extracted with EtOAc (2×25 mL). The combined organic phases were dried over $Na_2SO_4$, filtered and concentrated under reduced pressure to give a brown oil. The crude product was purified on an AnaLogix chromatography system eluting with 33-50% EtOAc/heptanes to give 680 mg (54%, greater than 98% purity) of 19 as a colorless oil.

Synthesis of (S)-6-(3-chloro-2-fluorobenzyl)-7-fluoro-1-(1-hydroxy-3-methylbutan-2-yl)-4-oxo-1,4-dihydroquinoline-3-carboxylic acid (20). To a solution of 19 (270 mg, 0.52 mmol) in 2-propanol (5 mL) was added 4N sodium hydroxide (1 mL) and the solution was stirred at rt for 3 h. The reaction mixture was acidified with 2N HCl (10 mL) and extracted with EtOAc (15 mL). The phases were separated and the aqueous phase was extracted with EtOAc (15 mL). The combined organic solution was dried over $Na_2SO_4$, filtered and concentrated under reduced pressure to give 220 mg (95%, 98% purity) of 20 as a white solid.

Synthesis of (S)-6-(3-Chloro-2-fluorobenzyl)-1-(1-hydroxy-3-methylbutan-2-yl)-7-(methoxy-d$_3$)-4-oxo-1,4-dihydroquinoline-3-carboxylic acid (112). Sodium (90 mg, 3.9 mmol) was added to CD$_3$OH (Cambridge Isotopes, 99.5 atom % D) (1 mL) at 0° C. After stirring for 0.5 h, the mixture was warmed to rt and stirred until the sodium had dissolved (approximately 2 h). The solution of NaOCD$_3$/CD$_3$OH was added to a solution of 20 (180 mg, 0.41 mmol) in CD$_3$OH (2 mL) and the mixture was stirred at rt for 1 h. The mixture was then heated at 65° C. for 3 h at which time LCMS showed the reaction was complete. The mixture was cooled to rt, acidified with 2N HCl (10 mL) and extracted with EtOAc (2×15 mL). The combined organic phases were dried over Na$_2$SO$_4$, filtered and concentrated under reduced pressure. The crude product was purified on an AnaLogix chromatography system with 3-5% MeOH/DCM to give 60 mg (32%, 98% purity) of 112 as a white gel-like solid. $^1$H-NMR (300 MHz, DMSO-d$_6$): δ 0.72-0.74 (m, 3H), 1.15-1.17 (m, 4H), 3.75-3.81 (m, 1H), 3.98-4.02 (m, 1H), 4.12 (s, 2H), 4.82-4.90 (m, 1H), 5.17-5.21 (m, 1H), 7.16-7.27 (m, 2H), 7.46-7.51 (m, 2H), 8.04 (s, 1H), 8.88 (s, 1H), 15.43 (s, 1H). HPLC (method: 20 mm C18-RP column—gradient method 2-95% ACN+0.1% formic acid in 3.3 min with 1.7 min hold at 95% ACN; Wavelength: 254 nm): retention time: 3.82 min; 98% purity. MS (M+H): 451.2.

Evaluation of Metabolic Stability

Certain in vitro liver metabolism studies have been described previously in the following references, each of which is incorporated herein in their entirety: Obach, R S, Drug Metab Disp, 1999, 27:1350; Houston, J B et al., Drug Metab Rev, 1997, 29:891; Houston, J B, Biochem Pharmacol, 1994, 47:1469; Iwatsubo, T et al., Pharmacol Ther, 1997, 73:147; and Lave, T, et al., Pharm Res, 1997, 14:152.

Microsomal Assay: Human liver microsomes (20 mg/mL) were obtained from Xenotech, LLC (Lenexa, Kans.). β-nicotinamide adenine dinucleotide phosphate, reduced form (NADPH), magnesium chloride (MgCl$_2$), and dimethyl sulfoxide (DMSO) were purchased from Sigma-Aldrich.

Determination of Metabolic Stability: 7.5 mM stock solutions of test compounds are prepared in DMSO. The 7.5 mM stock solutions are diluted to 50 μM in acetonitrile (ACN). The 20 mg/mL human liver microsomes are diluted to 0.625 mg/mL in 0.1 M potassium phosphate buffer, pH 7.4, containing 3 mM MgCl$_2$. The diluted microsomes are added to wells of a 96-well deep-well polypropylene plate in triplicate. 10 μL of the 50 μM test compound is added to the microsomes and the mixture is pre-warmed for 10 minutes. Reactions arere initiated by addition of pre-warmed NADPH solution. The final reaction volume is 0.5 mL and contains 1 mg/mL human liver microsomes, 1 μM test compound, and 2 mM NADPH in 0.1 M potassium phosphate buffer, pH 7.4, and 3 mM MgCl$_2$. The reaction mixtures are incubated at 37° C., and 50 μL aliquots are removed at 0, 5, 10, 20, and 30 minutes and added to shallow-well 96-well plates which contained 50 μL of ice-cold ACN with internal standard to stop the reactions. The plates are stored at 4° C. for 20 minutes after which 100 μL of water is added to the wells of the plate before centrifugation to pellet precipitated proteins. Supernatants are transferred to another 96-well plate and analyzed for amounts of parent remaining by LC-MS/MS using an Applied Bio-systems API 4000 mass spectrometer.

Data analysis: The in vitro t$_{1/2}$s for test compounds are calculated from the slopes of the linear regression of % parent remaining (ln) vs incubation time relationship.

in vitro $t_{1/2}$=0.693/k k=−[slope of linear regression of % parent remaining(ln) vs incubation time]

Data analysis is performed using Microsoft Excel Software.

The metabolic stability of compounds of Formula I is tested using pooled liver microsomal incubations. Full scan LC-MS analysis is then performed to detect major metabolites. Samples of the test compounds, exposed to pooled human liver microsomes, are analyzed using HPLC-MS (or MS/MS) detection. For determining metabolic stability, multiple reaction monitoring (MRM) is used to measure the disappearance of the test compounds. For metabolite detection, Q1 full scans are used as survey scans to detect the major metabolites.

SUPERSOMES™ Assay. Various human cytochrome P450-specific SUPERSOMES™ are purchased from Gentest (Woburn, Mass., USA). A 1.0 mL reaction mixture containing 25 pmole of SUPERSOMES™, 2.0 mM NADPH, 3.0 mM MgCl, and 1 μM of a compound of Formula I in 100 mM potassium phosphate buffer (pH 7.4) is incubated at 37° C. in triplicate. Positive controls contain 1 μM of elvitegravir instead of a compound of formula I. Negative controls used Control Insect Cell Cytosol (insect cell microsomes that lacked any human metabolic enzyme) purchased from GenTest (Woburn, Mass., USA). Aliquots (50 μL) are removed from each sample and placed in wells of a multi-well plate at various time points (e.g., 0, 2, 5, 7, 12, 20, and 30 minutes) and to each aliquot is added 50 μL of ice cold acetonitrile with 3 μM haloperidol as an internal standard to stop the reaction.

Plates containing the removed aliquots are placed in −20° C. freezer for 15 minutes to cool. After cooling, 100 μL of deionized water is added to all wells in the plate. Plates are then spun in the centrifuge for 10 minutes at 3000 rpm. A portion of the supernatant (100 μL) is then removed, placed in a new plate and analyzed using Mass Spectrometry.

Without further description, it is believed that one of ordinary skill in the art can, using the preceding description and the illustrative examples, make and utilize the compounds of the present invention and practice the claimed methods. It should be understood that the foregoing discussion and examples merely present a detailed description of certain preferred embodiments. It will be apparent to those of ordinary skill in the art that various modifications and equivalents can be made without departing from the spirit and scope of the invention. All the patents, journal articles and other documents discussed or cited above are herein incorporated by reference.

What is claimed is:

1. A compound of Formula I:

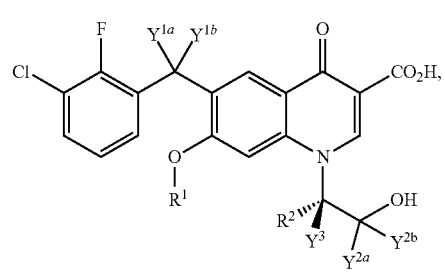

wherein:
each Y is independently selected from hydrogen and deuterium;
R$^1$ is selected from CH$_3$, CH$_2$D, CHD$_2$ and CD$_3$;

R² is an isopropyl group optionally containing 1 to 7 deuterium atoms; and when each Y is hydrogen, at least one R contains a deuterium atom, wherein the compound is compound 107 set forth in the table below:

| Compound | R¹ | R² | $Y^{1a}$ | $Y^{1b}$ | $Y^{2a}$ | $Y^{2b}$ | $Y^3$ |
|---|---|---|---|---|---|---|---|
| 107 | CH₃ | (CD₃)₂CD— | H | H | D | D | D | or a pharmaceutically acceptable salt thereof, wherein any atom not designated as deuterium is present at its natural isotopic abundance.

2. A pyrogen-free pharmaceutical composition comprising a compound of claim 1 or a pharmaceutically acceptable salt thereof, and a pharmaceutically acceptable carrier.

3. The composition of claim 2 further comprising a second therapeutic agent useful in the treatment of HIV infection.

4. The composition of claim 3, wherein the second therapeutic agent is selected from the group consisting of: ritonavir; darunavir; tipranavir; and any combination thereof.

5. A method of inhibiting the activity of HIV integrase in a cell infected with an HIV virus, comprising contacting the cell with a compound of claim 1 or a pharmaceutically acceptable salt thereof.

6. A method of treating HIV infection in a patient in need thereof comprising the step of administering to the patient an effective amount of a compound of claim 1 or a pharmaceutically acceptable salt thereof.

7. The method of claim 6, further comprising co-administering to the patient in need thereof a second therapeutic agent useful in the treatment of HIV infection.

8. The method of claim 7, wherein the second therapeutic agent is selected from the group consisting of: ritonavir; darunavir; tipranavir; and any combination thereof.

* * * * *